United States Patent [19]

Gettig et al.

[11] Patent Number: 5,215,535
[45] Date of Patent: Jun. 1, 1993

[54] NEEDLE PROTECTOR APPARATUS

[75] Inventors: William A. Gettig; Larry E. Shook, both of Millheim, Pa.

[73] Assignee: Gettig Technologies Incorporated, Spring Mills, Pa.

[21] Appl. No.: 885,844

[22] Filed: May 20, 1992

[51] Int. Cl.$^5$ ............................................. A61M 5/32
[52] U.S. Cl. ..................................... 604/198; 604/263
[58] Field of Search ............... 604/198, 187, 263, 192, 604/110

[56] References Cited

U.S. PATENT DOCUMENTS

| | | | |
|---|---|---|---|
| 4,631,057 | 12/1986 | Mitchell | 604/198 |
| 4,790,827 | 12/1988 | Haber et al. | 604/198 |
| 4,850,994 | 7/1989 | Zerbst et al. | 604/198 |
| 4,923,447 | 5/1990 | Morgan | 604/263 X |
| 4,927,416 | 5/1990 | Tomkiel | 604/198 |
| 4,931,048 | 6/1990 | Lopez | 604/110 |
| 4,998,920 | 3/1991 | Johnson | 604/198 |
| 5,011,479 | 4/1991 | Le et al. | 604/198 |
| 5,024,616 | 6/1991 | Ogle, II | 604/192 |
| 5,045,066 | 9/1991 | Scheuble et al. | 604/198 |
| 5,057,079 | 10/1991 | Tiemann et al. | 604/110 |
| 5,098,400 | 3/1992 | Crouse et al. | 604/192 |

Primary Examiner—John D. Yasko
Attorney, Agent, or Firm—Richard C. Litman

[57] ABSTRACT

A protective assembly for use with needle-bearing injector devices includes a pair of cylindrical sleeve members, initially concentrically disposed relative one another and adapted to be fitted about a conventional hypodermic syringe assembly. Prior to use of the injector device, the protective assembly is slipped over the needle, which is preferably covered by a sheath, until a latch mechanism on an inner one of the sleeves becomes locked between the hub of the needle and the forward portion of the syringe barrel. Following use of the injector device, an outer one of the sleeves is displaced forwardly until a latch mechanism adjacent its rear portion snap-fits within a catch provision on the forward portion of the inner sleeve, thus providing a post-use position wherein the syringe needle is fully peripherally surrounded by the extension of the outer sleeve. Both catch mechanisms are constructed to forestall reverse manipulation of either sleeve member so that not only is the possibility of needle sticks discouraged but also, reuse of the injector device is thwarted.

11 Claims, 3 Drawing Sheets

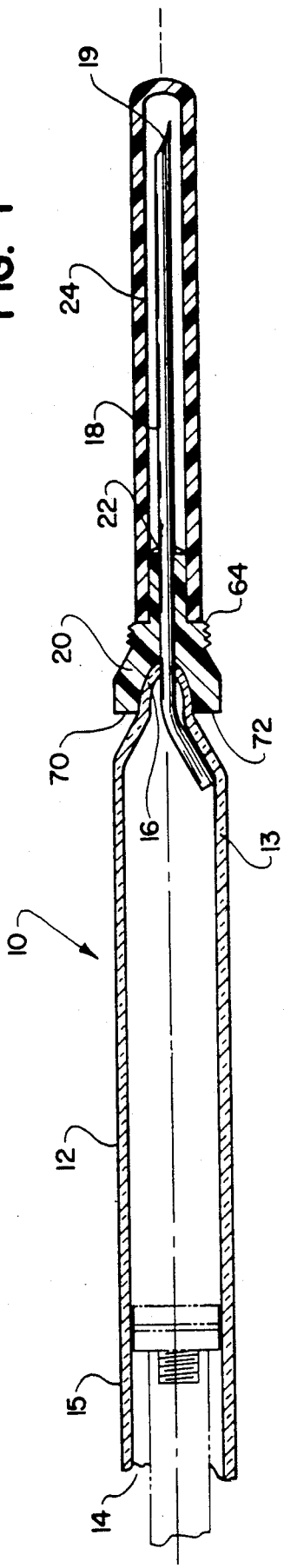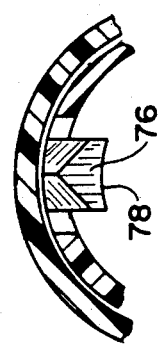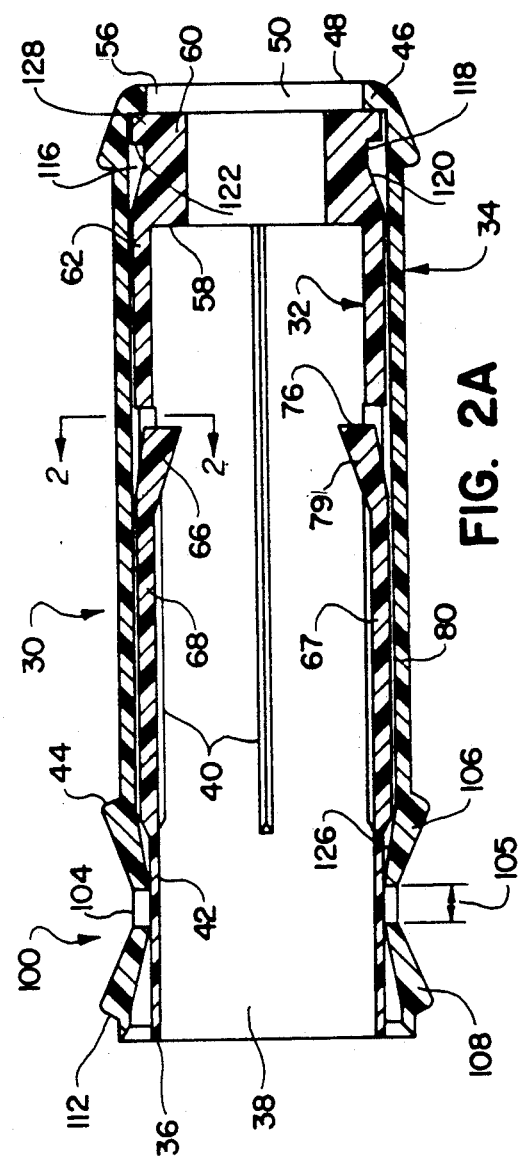

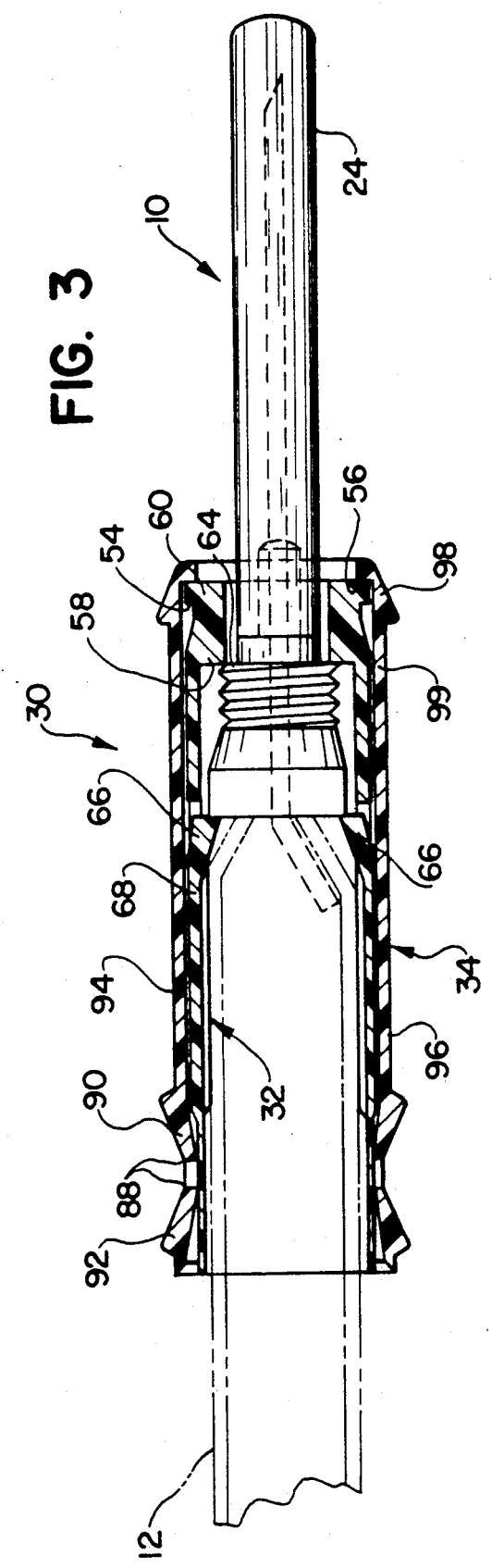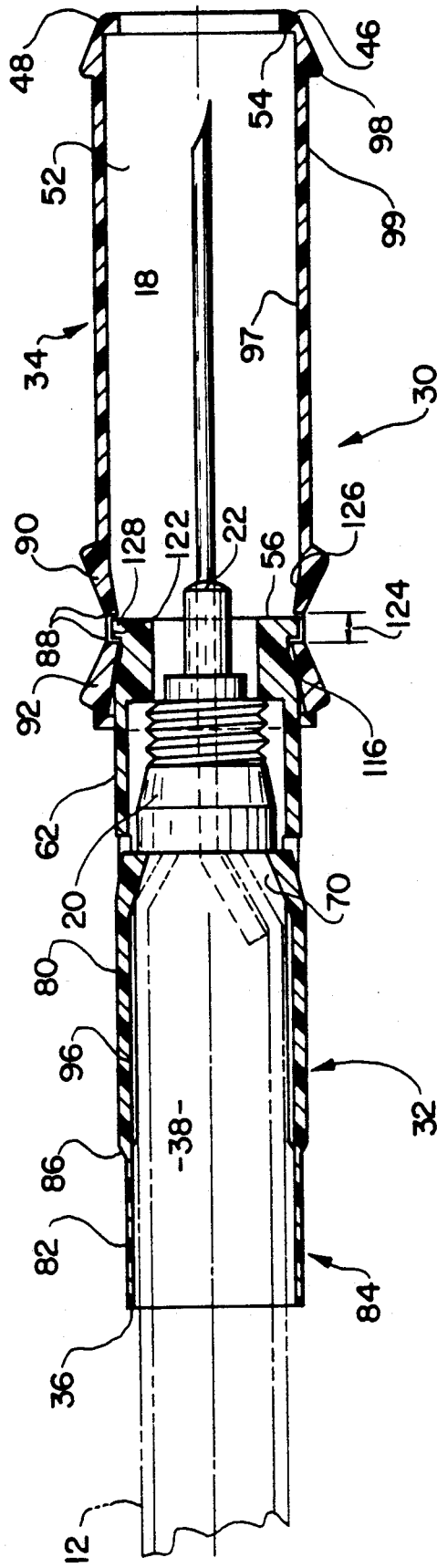

NEEDLE PROTECTOR APPARATUS

FIELD OF THE INVENTION

This invention relates generally to medical protective devices and more particularly, to an improved shielding apparatus for use with hypodermic syringes, cartridges or the like which include a needle or cannula thereon.

BACKGROUND OF THE INVENTION

In the medical profession, much concern is now exhibited by all personnel having anything to do with the multitude of sharps as constantly employed throughout all phases of medical examination and treatment. Unquestionably, the most prevalent implement among the several types of sharps comprises the common hypodermic syringe. Ever since the advent of this most popular method of administering medicament, needle sticks have presented a problem. The primary concern resides with the nurse or physician using the syringe but the danger of becoming infected by a needle stick does not halt at this level since other staff members are also at risk, such as janitorial personnel or others associated in any way in the disposal chain. Now, with the heightened awareness of the HIV virus, all the more emphasis is being placed upon the need to provide the highest degree of protection to all personnel exposed to injection devices employing invasive elements such as needles.

The most conventional type of medical injection apparatus comprises an elongated cartridge or barrel having a constricted forward nose upon which is affixed a hub device serving as part of the anchorage of the needle passing through the barrel nose. The ideal no-stick needle protective apparatus should comprise a simple, low-cost device that readily adapts to the above type of syringe assembly without requiring any modification thereof. The instant device meets this criteria by providing a two-part assembly that is snap-fitted to existing syringes, using the inherent structure thereof to anchor the assembly in an initial, pre-use position.

DESCRIPTION OF THE RELATED ART

Generally, it is well known to provide protective devices adapted to be attached to various types of medical apparatus for the purpose of offering shielding against needle sticks following use of the apparatus. Few such devices are constructed in a manner allowing of use with the more conventional types of injection members, without prior modification of the syringe or the like. U.S. Pat. No. 5,098,400 issued Mar. 24, 1992 to Crouse et al. depicts a protective shielding device usable with the common type of rubber sheath as frequently shrouding the exposed needle of a syringe assembly prior to its use. In this example, an elongated shield member having deflected tabs is rearwardly slipped over the previously applied rubber sheath to provide protection against the needle tip being forced through the sheath and sticking a user.

An example of a post-use protective device for syringes will be found in U.S. Pat. No. 4,931,048 issued Jun. 5, 1990 to Lopez and wherein a tubular guard member is carried by a syringe needle and shiftable between alternate positions respectively exposing and shielding the tip of the needle. Opposite ends of the guard device cooperate with a specifically constructed hub device and a locking element attached to the medial portion of the needle.

Sleeve members displaceable from a pre-use position about a syringe barrel to a post-use position enshrouding the needle, will be found in U.S. Pat. Nos. 4,790,827 issued Dec. 13, 1988 to Haber et al., 4,850,994 issued Jul. 25, 1989 to Zerbst et al. and 5,057,079 issued Oct. 15, 1991 to Tiemann et al. all of which involve a modification of the syringe barrel in order to accommodate catch elements on the sleeve member.

U.S. Pat. No. 4,998,920 issued to Johnson on Mar. 12, 1991 is directed to a syringe protective sleeve wherein a single collar device is affixed to the forward portion of a cartridge, behind the needle hub and serves to provide twist lock means retaining the displaceable sleeve in its pre-use and post-use positions.

The above prior art is not seen to suggest the present development wherein a protective assembly comprising a pair of concentric sleeves is adapted to be snap-fitted about a conventional syringe apparatus and is subsequently manipulated by slidably shifting an outermost one of the sleeves to an extended protective position wherein additional snap-fitting elements on the two sleeves retain the device in the post-use position.

SUMMARY OF THE INVENTION

By the present invention, an improved needle stick protective assembly is provided and which comprises two cooperating sleeves including an innermost mounting sleeve about which is captively disposed a slidable sleeve. In an initial condition, the mounting sleeve is substantially fully surrounded by the slidable sleeve and in this mode, the assembly is readily affixed to a conventional syringe of the type having a barrel terminating in a forward nose to which is attached a needle hub. With these syringes, an annular space is formed between the rear of the needle hub and the front of the cartridge or barrel and this annular clearance presents a ring abutment or shoulder at the rear of the needle hub that serves to anchor the protective assembly as it is slipped over the barrel prior to use. Following use of the syringe, the protective device is activated by axially displacing the outermost slidable sleeve in a forward direction. This displacement is limited by resilient catch members adjacent the rear of the outer sleeve and which automatically engage within an annular groove within the forward portion of the mounting sleeve, to secure the relatively extended sleeves in the post-use position. In this mode, the needle is fully peripherally surrounded or shielded by the slidable sleeve.

Accordingly, one of the objects of the present invention is to provide an improved protective assembly adapted to be attached to existing syringe devices without any modification thereof.

Another object of the present invention is to provide an improved protective assembly for injector devices including a pair of initially concentrically disposed sleeve members respectively having latch means providing for attachment to a syringe assembly and between the two sleeve members when axially displaced relative one another.

A further object of the present invention is to provide an improved protective assembly for a syringe assembly including an inner mounting sleeve having catch means snap-fitting behind the needle hub of the syringe and slidably supporting an outer sleeve shiftable forwardly to a locked position enshrouding the syringe needle after use of the syringe. objects of the present invention is to provide an improved protective assembly Still another object of the present invention is to provide an improved protective assembly for injector devices including an inner sleeve provided with deflectable tabs engageable behind the needle hub of a syringe assembly to retain the sleeve thereon while an outer shiftable sleeve surrounding the inner sleeve is subsequently displaceable only in a forward direction to surround the full length of the needle, as other deflectable tabs engage a catch in the inner sleeve to retain the outer sleeve in its extended, protective position.

With these and other objects in view which will more readily appear as the nature of the invention is better understood, the invention consists in the novel construction, combination and assembly of parts hereinafter more fully described, illustrated and claimed with reference being made to the attached drawings.

BRIEF DESCRIPTION OF THE DRAWINGS

FIG. 1 is a side elevation of a typical off-the-shelf syringe assembly with which the present device may be used;

FIG. 2 is a side elevation of the protective assembly of the present invention, shown in the collapsed condition prior to application to a syringe such as shown in FIG. 1;

FIG. 2A is a fragmentary sectional view, taken along the line 2—2 of FIG. 2;

FIG. 3 is a side elevation of the syringe of FIG. 1 with the protective assembly of FIG. 2 attached thereto to provide a pre-use condition;

FIG. 4 is a side elevation as in FIG. 3 but with the protective assembly shifted and as it appears in the protective, post-use position;

Similar reference characters designate corresponding parts throughout the several figures of the drawings.

DESCRIPTION OF THE PREFERRED EMBODIMENT

Figure 5:
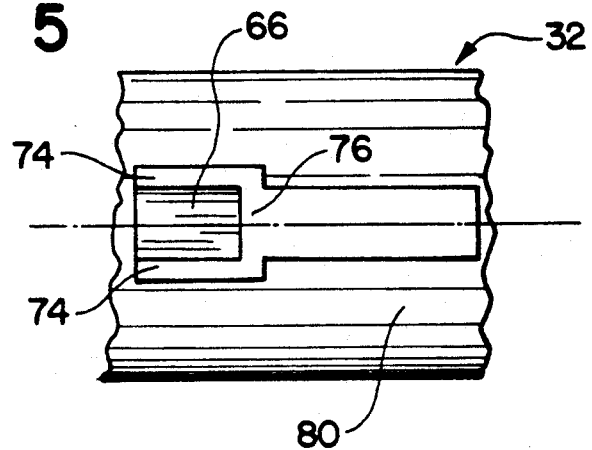
FIG. 5 is a fragmentary top plan view of the left hand portion of FIG. 2A.
Figure 6:
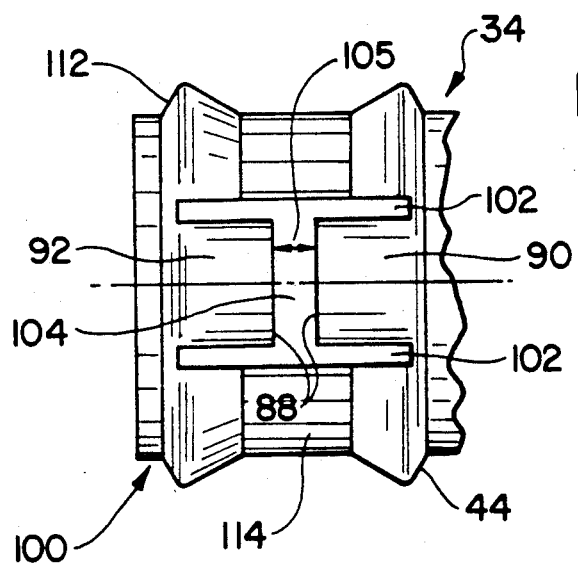
FIG. 6 is a fragmentary top plan view of one of the attachment tabs on the inner sleeve.

Referring now to the drawings, particularly FIG. 1, the present invention will be understood to relate to a protective assembly adapted to be used with a typical syringe assembly 10 and which includes a cylindrical cartridge or barrel 12 having a rear, open end 14 and a forward, restricted end defining a nose portion 16 through which is disposed a cannula or needle 18. As is common, an apertured hub 20 is placed over the tip of the nose portion 16 and this hub, together with the needle 18, is secured relative the cartridge nose, by any suitable sealant composition 22. The earliest attempt at providing protective devices for syringe assemblies comprises the use of a cap or sheath 24 about the exposed needle 18. This sheath is usually fabricated of rubber and primarily serves to maintain the sterility and sharpness of the needle prior to the syringe being used. Users rarely expect to benefit from any post-use protection by re-applying this sheath 24 in view of the risk of attempting to re-attach the sheath to a contaminated needle. It is during this very maneuver that a user could be bumped in the elbow or otherwise struck in a manner leading to a needle stick. Even with an uneventful reattachment of the sheath 24, little effort is required to force the tip of the needle through the soft rubber of most of these sheaths, Thus, a more positive and reliable apparatus must be utilized to provide an acceptable degree of protection against accidental needle sticks and which will also act to deter the unauthorized re-use of the syringe assembly.

The needle protective assembly 30 shown most clearly in FIG. 2 of the drawings comprises a two-part device which is readily attached to existing syringe assemblies, such as the syringe 10 shown in FIG. 1, without requiring any modification thereof. The assembly 30 comprises two elongated, cylindrical sleeves constructed of suitable material such as any of several synthetic resinous products which exhibit at least a minimal degree of resilience, for reasons which will become obvious hereinafter. As initially delivered to the end user, the assembly 30 will appear as in this drawing view, wherein an inner or mounting sleeve 32 is nested within an outer or slidable sleeve 34. While still in this concentric relationship, the assembly 30 is attached to the intended syringe 10 prior to administering the medicament (not shown) as contained within the barrel 12. During this manipulation, the rear face 36 of the inner or mounting sleeve 32 is slipped over the tip 19 of the needle 18 and the bore 38 of this sleeve passed rearwardly until it surrounds the forward portion 13 of the barrel 12. For maximum protection during this operation and to maintain a sterile condition, the sheath 24 remains about the needle 18. This discourages any needle stick of the attending personnel which could in turn cause contamination of the heretofore sterile syringe assembly, should that party exhibit an infectious agent.

Slipping of the bore 38 of the inner sleeve over the periphery of the syringe barrel 12 is facilitated by the provision of a plurality of inwardly directed, longitudinally extending ribs or beads 40 on the inner surface 42 forming the bore 38. With four such beads equispaced about the surface 42, it will be appreciated that a stabilized, minimum frictional engagement is assured during this axial displacement of the protective assembly 30.

The above rearward displacement occurs as one grasps the outer slidable sleeve 34 and urges it backwards. A positive grip is assured in view of the outwardly projecting front ridge 44 and against which one may urge their thumb and forefinger. Rearward movement of this outer sleeve 34 results in a corresponding, simultaneous rearward movement of the inner sleeve 32 in view of the inwardly directed flange or lip 46 adjacent the front edge 48 of the outer sleeve 34. This lip defines a reduced diameter opening 50 leading to the outer sleeve bore 52 that surrounds the inner sleeve 32. With this construction, as the assembly 30 of FIG. 2 is moved past the needle and onto the barrel 12 as in FIG. 3, it will be seen that this rearward motion as imparted to the outer sleeve 34 is transferred as a concurrent displacement of the inner sleeve 32 as the shoulder 54 of the lip 46 abuts and urges the front face 56 of the inner sleeve 32.

The attachment of the protective assembly 30 to the syringe assembly 10 is completed as the rearwardly facing shoulder 58 of a reduced diameter inner ring 60 on the forward portion 62 of the inner sleeve strikes the front surface 64 of the needle hub 20. At the time of this abutment, attachment means in the form of a pair of inwardly directed diametrically opposed tabs, fingers or latches 66 come into play. These tabs are integral with and cut out from the main body portion 67 of the cylindrical wall 68 of the mounting sleeve 32 and radially snap-fit into the annular clearance 70 existing intermediate the rear surface 72 of the needle hub 20 and the main body of the syringe barrel 12. The tabs 66 will be seen to be attached at their rear to the sleeve wall 68 and are formed by lateral, longitudinally extending cut-outs or slots 74, presenting a forwardly directed end face 76 to the tabs. Each of these tabs 66 is constructed with a triangular cross-section when viewed transversely and with a maximum mass adjacent the end face 76. With this configuration, the tabs are formed at an inward inclination of substantially 20 degrees with the lower or innermost portion 78 of each tab presenting a sharp free edge or line disposed well within the sleeve bore 38. Typically, these tabs 66 are inclined downwardly approximately 20 degrees relative the sleeve inner surface 42. With the above in mind, the operation of the assembly 34 as it is slipped over the needle 18 and onto the barrel 12, will be readily appreciated as it is understood that initially, the inner surface 79 of the inner sleeve tabs 66 will strike the needle hub 20 and be cammed thereover as the assembly 34 is moved rearwardly. Just as the end faces 76 of the tabs clear the hub rear surface 72, the inherent resilience of the tabs causes them to snap radially inwardly, into the annular clearance 70 behind the hub 20. In this manner, the assembly 30 is precluded from any forward movement while the inner sleeve shoulder 58 is juxtaposed the forward portion 64 of the needle hub 20, thereby captively retaining the protective assembly 30 upon the syringe assembly 10.

With the protective assembly 30 attached to the syringe assembly 10 as shown in FIG. 3, the apparatus is ready for use, either to administer a pre-loaded medicament or to fill the syringe with a prescribed volume of medicament. To accomplish the actual injection, the usual procedure is carried out, following removal of the sheath 24. Immediately thereafter, the user grasps the rear portion 15 of the barrel, behind the protective assembly 30, with one hand and then with the other hand, axially displaces the outer, sliding sleeve 34 in a forward direction, to the post-use position of FIG. 4.

Details of the construction and operation of the outer sleeve 34 will now be explained, along with its cooperation with the stationary mounting sleeve 32. As shown most clearly in FIG. 4, the majority of the axial extent of the mounting sleeve 32 defines an outer surface 80 having a greater diameter than the reduced diameter outer surface 82 of the rear portion 84 adjacent the rear face 36. At the juncture of these two surfaces 80,82 is formed a ridge or ramp 86 presenting a nominal inclined abutment between the two outer surfaces of the sleeve. Preferably the inclination of this ramp ranges between 25-35 degrees from the vertical, with 30 degrees having been found quite acceptable. With this construction, and the outer, slidable sleeve 34 in the collapsed condition of FIGS. 2 and 3, it will be seen that the edges 88 of latch means in the form of two pairs of opposed tabs or fingers 90,92 on the outer sleeve are engaged with the outer surface 82 of the inner sleeve rear portion 84. In this manner the outer sleeve 34, when in the pre-use condition with its forward shoulder 54 abutting the inner sleeve front face 56, will be understood to be retained against unwanted forward displacement. This will be due to the engagement of either the front tabs 90 or rear tabs 92 against the inner sleeve ramp 86 and which provides a resistance against unaided movement of the outer sleeve forwardly. At all times, the inherent resilience of the material of the sleeve 34 and its integral tabs, insures that the tabs edges 88 are biased toward their normal, at-rest position radially spaced inwardly of the sleeve inner surface 97.

On the other hand, following administration of the medicament in the syringe assembly and when it is desired to activate the protective mode of the assembly 30, a user merely grasps the outer surface 94 of the sleeve cylindrical wall 96 and displaces it forwardly until the outer sleeve is in the post-use position of FIG. 4. Aiding in this maneuver is the outwardly directed ring or flange 98 on the forward portion 99 and which offers an abutment for the user's fingers while sliding the outer sleeve forwardly.

During the initial above forward movement, only a nominal degree of force is required to overcome the resistance offered by the inner sleeve ramp 86 to the pairs of outer sleeve tabs 90 and 92. The inclination of the ramp 86 and the fact that the difference in diameters between the outer surfaces 80 and 82 is approximately 0.030 inches, will be seen to result in a minimal obstruction to the sliding of the outer sleeve. The two pairs of tabs 90 and 92 comprise integral elements of the outer sleeve and are formed in the rear portion 100 of the sleeve and between pairs of parallel, longitudinally extending slots 102, 102 communicating with a transverse opening or slot 104. The width of this slot 104 or, the distance 105 between the opposed edges 88-88 of each pair of tabs 90,92 is calculated to cooperate with catch means on the inner sleeve, as will soon be described. The sleeve rear portion 100 includes two thickened annular sections, namely a front section 106 and a rear section 108, respectively presenting the outwardly directed front ridge 44 and a rear ridge 112, joined to an intermediate cylindrical wall 114. With this construction in mind, it will be appreciated that ready means are provided for a user to grasp the outer sleeve with two fingers, in the area of the intermediate wall 114 and which presents a smaller diameter than the two adjacent sections 106,108.

As the outer sleeve is displaced forwardly from the pre-use position and the tab edges 88 have been cammed or urged outwardly by the ramp 86, it will be understood that these resilient tabs will be biased against the inner sleeve outer surface 80. During the continued forward displacement, these tabs slide over the inner sleeve surface as the outer sleeve front edge 48 progressively moves toward and then beyond the tip 19 of the syringe needle. When the outer sleeve rear portion 100 approaches the inner sleeve forward portion 62, stop or catch means comprising an annular groove 116 adjacent the inner sleeve front face 56, comes into play to halt the forward displacement of the outer sleeve and lock it into the protective post-use position of FIG. 4.

The catch groove 116 will be seen to be formed by a reduced diameter ring section 118 and which communicates with the sleeve cylindrical outer surface 80 by means of a frustoconical surface or ramp 120. The forward extent of the groove 116 is defined by a radial face or shoulder 122 axially spaced from the sleeve front face 56 a distance 124 which is slightly less than the distance 105 between the pairs of opposed outer sleeve tabs 90,92. Accordingly, as the outer sleeve tabs reach the forward portion 62 of the inner sleeve, the edge 88 of the forward tabs 90,90 initially will be biased inwardly as they slide down the ramp 120. Continued displacement of the outer sleeve then causes the shoulder 122 of the inner sleeve to engage the inside surface 126 of the tabs 90 and deflect them outwardly. At this point, the edges 88 of the rear tabs 92 are biased inwardly as they slide down the ramp 120. Further forward displacement ceases when these latter tab edges 88 abut the shoulder 122, just after the forward tabs 90,90 have snapped inwardly, juxtaposed the inner sleeve front face 56. With this disposition, it will be appreciated that the flanged section 128 as formed between the groove 116 and front face 56, will be sandwiched between the edges 88,88 of the pairs of inwardly directed tabs 90,92.

In the above post-use position of FIG. 4, the two sleeves are locked in the extended condition and in turn remain locked relative the syringe assembly, as the radial faces 88 of the pairs of tabs 90,92 captively engage the radial surfaces 56, 122 of the flanged section 128.

From the above, it will be appreciated that an improved needle stick protector apparatus is presented and wherein an assembly of two relatively slidable sleeves is readily affixed to a conventional syringe assembly and thereafter, quickly and simply manipulated to extend an outer one of the sleeves to a post-use, needle shrouding position. The foregoing is achieved without any prior modification of the syringe assembly and additionally provides a deterrent against unauthorized reuse of the syringe.

It is to be understood that the present invention is not limited to the sole embodiment described above, but encompasses any and all embodiments within the scope of the following claims.

We claim:

1. In a needle protective assembly adapted to fixedly engage a syringe assembly having a needle and hub directly secured to a cartridge provided with a nose portion and wherein the hub includes front and rear surfaces with the latter adjacent a reduced diameter annular clearance formed by the cartridge nose, the improvement comprising;
   an inner sleeve having opposite front and rear faces and including an axial bore surrounded by an inner surface, a reduced diameter inner ring on said inner sleeve adjacent said front face, stop means comprising a rearwardly facing shoulder on said reduced diameter inner ring,
   attachment means on said inner sleeve intermediate said front and rear faces and adapted to engage a syringe assembly hub when said rear face and inner surface is slipped over a syringe assembly cartridge, said attachment means including an inwardly directed resilient tab normally biased toward said bore,
   an outer sleeve having opposite forward and rearward portions and including an inner surface slidable over said inner sleeve from a pre-use position substantially fully surrounding said inner sleeve to a post-use position wherein said outer sleeve enshrouds the syringe assembly needle,
   said inner and outer sleeves retained upon the syringe assembly cartridge with said inner sleeve resilient tab disposed within the reduced diameter annular clearance and abutting the rear surface of the hub while said rearwardly facing shoulder abuts the front surface of the hub to captively engage the hub and preclude axial displacement of said inner sleeve relative the syringe assembly,
   latch means comprising a pair of axially opposed and inwardly directed resilient fingers on said outer sleeve adjacent said rearward portion initially biasingly engaging said inner sleeve and retaining said outer sleeve substantially fully surrounding said inner sleeve to maintain said pre-use position, and
   catch means on said inner sleeve adjacent said front face and engageable by said outer sleeve latch means when said outer sleeve is axially displaced forwardly relative said inner sleeve, said catch means including a flange section and an adjacent annular groove whereby
   engagement between said inner sleeve catch means and outer sleeve latch means axially locks said sleeves in a relatively extended post-use position with said flange section captively disposed intermediate said pair of resilient fingers.

2. A needle protective assembly according to claim 1 wherein,
   said fingers include a forwardly facing rear finger and a rearwardly facing front finger spaced from said forwardly facing rear finger and defining a transverse slot therebetween.

3. A needle protective assembly according to claim 1 including,
   a plurality of longitudinally extending ribs on said inner surface of said inner sleeve.

4. A needle protective assembly according to claim 1 wherein,
   said inner and outer sleeves are formed of a synthetic resinous composition.

5. A needle protective assembly according to claim 1 wherein,
   said inner sleeve includes a main body and a rear portion, and
   said outer sleeve latch means engageable with said inner sleeve rear portion when said inner and outer sleeves are in said pre-use position.

6. A needle protective assembly according to claim 4 wherein,
   said inner sleeve attachment means and said outer sleeve latch means comprise integral portions of said inner and outer sleeves respectively.

7. A needle protective assembly according to claim 4 wherein,
   said synthetic resinous composition exhibits a minimal degree of resilience.

8. A needle protective assembly according to claim 4 including,
   a pair of said tabs and tab having free edges directed toward said inner sleeve front face.

9. A needle protective assembly according to claim 5 including,
   an outer surface on said inner sleeve main body and rear portion, and
   said rear portion outer surface defines a smaller diameter than said main body.

10. A needle protective assembly according to claim 9 including,
    a ramp disposed intermediate said outer surfaces of said main body and rear portion.

11. A needle protective assembly according to claim 2 including,
    a pair of said front and rear fingers arcuately spaced apart from one another.

* * * * *